United States Patent [19]
Schach et al.

[11] Patent Number: 5,917,037
[45] Date of Patent: Jun. 29, 1999

[54] PROCESS FOR THE PREPARATION OF N-CARBOXYALKYL-3-FLUORO-4-DIALKYLAMINOANILINES

[75] Inventors: Thomas Schach, Gernsheim; Theodor Papenfuhs, Frankfurt, both of Germany

[73] Assignee: Clariant GmbH, Frankfurt, Germany

[21] Appl. No.: 09/035,427

[22] Filed: Mar. 5, 1998

[30] Foreign Application Priority Data

Mar. 7, 1997 [DE] Germany .......................... 197 09 439
Mar. 7, 1997 [DE] Germany .......................... 197 09 441
Mar. 7, 1997 [DE] Germany .......................... 197 09 442

[51] Int. Cl.$^6$ ................................................. C07D 295/14
[52] U.S. Cl. ........................... 544/166; 544/393; 544/395; 546/232; 546/233; 546/234; 560/30; 560/31
[58] Field of Search ..................................... 544/166, 393; 560/31

[56] References Cited

FOREIGN PATENT DOCUMENTS

WO 95/25106  9/1995  WIPO .
WO 96/23788  8/1996  WIPO .

OTHER PUBLICATIONS

European Search Report
Steven J. Brickner et al. "Synthesis Antibacterial Activity of U–100592 and U100766, Two Oxazolidinone Antibacterial Agents for the Potential Treatment of Multidrug–Resistant Gram–Positive Bacterial Infections" Journal of Medicinal Chemistry, Bd. 39, Nr. 3, Feb. 2, 1996, Washington, US.
Rene Beugelmans et al. "Snythese d heterocycles a 5 et 6 chainons par une strategie combinant des reactions SNAr et SRN1" Bulletin de la Societe Chimique de France., Bd. 132, Nr. 3, 1995, Paris FR, Seiten 306–313, XP002070210.
Violetta Cecchetti et al. "1,4–Benzothiazine–2–carboxylic Acid 1–Oxides as Analogues of Antibacterial Quinolones '1!" Journal of Heterocyclic Chemistry., Bd 29, Nr. 2, 1992, Provo US, Seiten 375–382, XP002070211.

*Primary Examiner*—Robert W. Ramsuer
*Attorney, Agent, or Firm*—Scott E. Hanf

[57] ABSTRACT

The present invention relates to a process for the preparation of N-carboxyalkyl-3-fluoro-4-dialkylaminoanilines, which comprises reacting, in a first step, an orthonitrochlorobenzene of the formula (1)

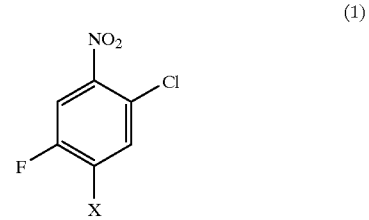

(1)

in which X is Cl or F, with a secondary amine of the formula (2) $HNR^1R^2$, in which $R_1$ and $R^2$, independently of one another, are identical or different and are an alkyl radical having from 1 to 10 carbon atoms or, together with the N atom to which they are bonded, form a ring having from 3 to 7 members, in the presence of a base in the presence or absence of a solvent at from −10 to 120° C., reacting, in a second step, the 2-chloro-4-dialkylamino-5-fluoronitrobenzene with hydrogen at from 30 to 150° C. and from 1 to 100 bar in the presence of a base and a noble-metal catalyst and, in a third step, extracting the 3-fluoro-4-dialkylaminoaniline from the reaction mixture using an aqueous solution of an acid as a salt dissolved in water, removing the aqueous phase and reacting the 3-fluoro-4-dialkylaminoaniline salt, dissolved in water, with a chloroformate of the formula (3) $ClCO_2R^3$, in which $R^3$ is an alkyl radical having from 1 to 10 carbon atoms or an aralkyl radical having from 7 to 20 carbon atoms, at from 0 to 100° C. in the presence of a basic compound.

13 Claims, No Drawings

PROCESS FOR THE PREPARATION OF N-CARBOXYALKYL-3-FLUORO-4-DIALKYLAMINOANILINES

The present invention relates to a process for the preparation of N-carboxyalkyl-3-fluoro4-dialkylaminoanilines which is improved compared with the prior art, and to the compounds 2-chloro-5-fluoro-4-(diethylamino-morpholino-, -piperidino- or -piperazino)nitrobenzene and 2-chloro-5-fluoro-4-(morpholino- or -piperazino)aniline.

N-Carboxyalkyl-3-fluoro-4-dialkylaminoanilines play an important role as intermediates in the preparation of pharmaceuticals (WO-95/25106).

As WO 95/25106 explains, N-carboxybenzyl-3-fluoro-4-piperidinoaniline is used as intermediate in the preparation of oxazolidinone derivatives and pharmaceutical compositions containing these derivatives.

To prepare N-carboxybenzyl-3-fluoro-4-piperidinoaniline (Example 1 of WO 95125106), 3,4-difluoronitrobenzene is reacted, in a first step, with piperidine in ethyl acetate in the presence of diisopropylethylamine, water is added to the reaction solution, and the ethyl acetate phase is separated off, washed with water and sodium chloride solution and dried over anhydrous sodium sulfate. The solvent is then evaporated off to give the nitro compound (3-fluoro-4-piperidinonitrobenzene). The nitro compound is dissolved in ethyl acetate and hydrogenated in the presence of a palladium catalyst, the catalyst is filtered off and the mixture is evaporated under reduced pressure to give the corresponding amine (3-fluoro-4-piperidinoaniline). In a third step the amine dissolved in tetrahydrofuran is reacted with sodium hydrogencarbonate and a chloroformate and, when the reaction is complete, water is added and the tetrahydrofuran solution is separated off, washed with water and sodium chloride solution and dried over anhydrous sodium sulfate. After the solvent has been evaporated off, the product is purified by column chromatography.

The synthesis described above makes use of the fact that the fluorine in the 4-position is replaced by a piperidine radical. It should, however, be noted that the 3,4-difluoronitrobenzene used as starting material has only one suitable position for the substitution reaction, namely the para-position activated by the nitro group. Since 3,4-difluoronitrobenzene has no other substitutable groups which are in the ortho-position relative to the nitro group, substitution of the fluorine in the 4-position proceeds smoothly and without any complications.

As is known, a nitro group activates halogen substituents in both the ortho- and the para-positions. For example, if 2-chloronitrobenzene is reacted with aniline at from 175 to 205° C., 2-nitrodiphenylamine is obtained in quantitative yield. By contrast, 4-chloronitrobenzene does not react at all with aniline at from 175 to 205° C.(Houben-Weyl, Methoden der Organischen Chemie [Methods of Organic Chemistry], IVth Edition, Volume XI/1, pages 63 and 64). This behavior shows that the nitro group activates the chlorine in the ortho- position to a very great extent, while its activating effect on the chlorine in the para-position is insufficient to permit the substitution reaction.

The process for the preparation of N-carboxybenzyl-3-fluoro-4-piperidinoaniline described in WO 95125106 has several disadvantages. Firstly, only one starting material, namely 3,4-difluoronitrobenzene, can be used and, secondly, 3,4-difluoronitrobenzene is a very expensive product which can only be prepared by a very complex, multi-stage synthesis. Other disadvantages are that the process requires a very large number of individual steps and each intermediate is isolated. Moreover, the individual reaction steps require a significant amount of time, the first stage requiring 2 days and the two other stages each requiring 14 hours.

In view of the above, there is a need to provide a process for the preparation of N-carboxyalkyl-3-fluoro4-dialkylaminonanilines which avoids the said disadvantages and which can be carried out with an acceptable labor and time expenditure. Moreover, this process should not be limited to the preparation of N-carboxyalkyl-3-fluoro-4-piperidinoanilines, but should make available other compounds from this group of substances.

This object is achieved by a process for the preparation of N-carboxyalkyl-3-fluoro-4-dialkylaminoanilines which comprises reacting, in a first step, an orthonitrochlorobenzene of the formula (1)

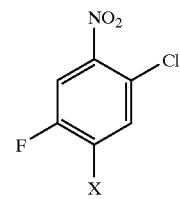

in which X is Cl or F, with a secondary amine of the formula (2) $HNR^1R^2$, in which $R^1$ and $R^2$, independently of one another, are identical or different and are an alkyl radical having from 1 to 10 carbon atoms or, together with the N atom to which they are bonded, form a ring having from 3 to 7 members, in particular from 5 to 7 members, in the presence of a base in the presence or absence of a solvent at from −10 to 120° C., reacting, in a second step, the 2-chloro4-dialkylamino-5-fluoronitrobenzene with hydrogen at from 30 to 150° C. and from 1 to 100 bar in the presence of a base and a noble-metal catalyst and, in a third step, extracting the 3-fluoro4-dialkylaminoaniline from the reaction mixture using an aqueous solution of an acid as a salt dissolved in water, removing the aqueous phase and reacting the 3-fluoro-4-dialkylaminoaniline salt, dissolved in water, with a chloroformate of the formula (3) $ClCO_2R^3$, in which $R^3$ is an alkyl radical having from 1 to 10 carbon atoms or an aralkyl radical having from 7 to 20 carbon atoms, at from 0 to 100° C. in the presence of a basic compound.

In view of the above comments on the reaction of 2-chloronitrobenzene and 4-chloronitrobenzene with aniline, which show that the chlorine substituent in the para-position relative to the nitro group has insufficient activation for a substitution reaction, it is very surprising that replacement of the substituent X which is in the para-position relative to the nitro group takes place in the ortho-nitrochlorobenzene of the formula (I) despite the presence of an ortho-chlorine substituent which is highly activated by the nitro group. In view of the above discussion regarding the differing activation, it would have been expected that merely the chlorine in the ortho-position would be replaced and that replacement of the substituent X in the para-position would not take place. It would not have been expected that in the case where X is Cl, any substitution would take place at all, let alone to an appreciable extent. Neither would it have been expected that in the case where X is F, the reaction takes place with high selectivity with replacement of the fluorine in the 4-position, while the chlorine in the ortho-position relative to the nitro group remains in the molecule.

An advantage of the process according to the invention is that it is possible to use two different starting materials, namely 2,4-dichloro-5-fluoronitrobenzene and 2-chloro4,5-difluoronitrobenzene and, moreover, both of these starting materials are significantly more readily available than 3,4-difluoronitrobenzene. It is also an advantage that, when carrying out the process according to the invention, it is not always necessary to isolate every intermediate before processing it further. Although it is possible to isolate the corresponding intermediates in order to process them further, it is, however, also advantageous to omit complex intermediary isolation and to subject the reaction mixture produced in each case to simple separation techniques (filtration, extraction) prior to processing it further and then to process it further directly.

The novel process for the preparation of N-carboxyalkyl-3-fluoro-4-dialkyl-aminoanilines is reproduced in simplified form by the following reaction scheme.

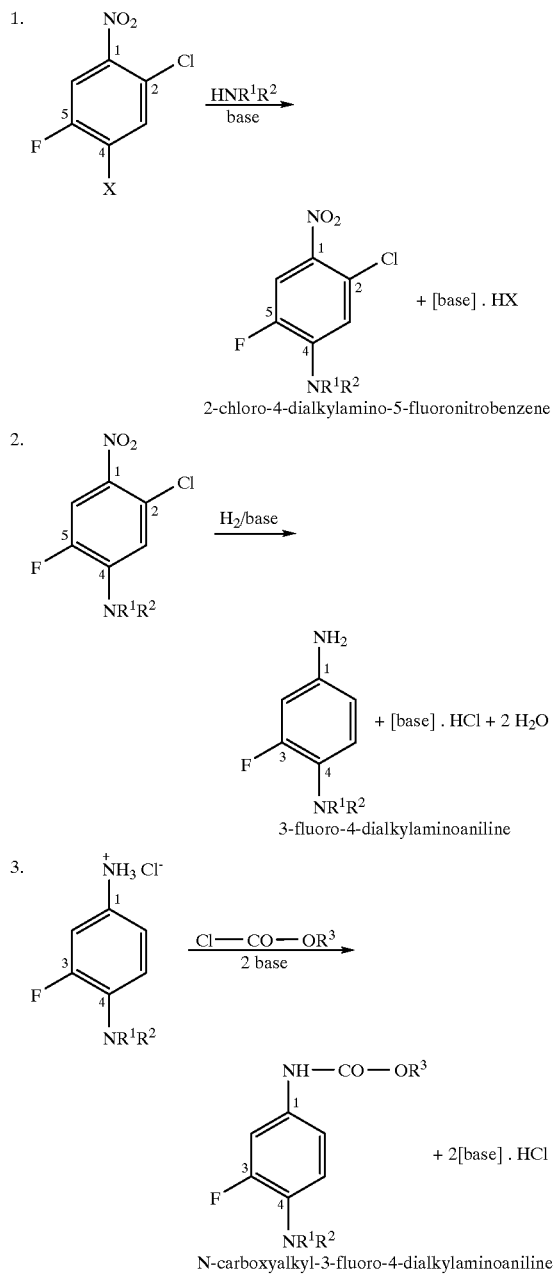

As already mentioned above, the substituent X in the para-position relative to the nitro group in ortho-nitrochlorobenzene of the formula (1) is replaced in a first step by an amine radical —NR$^1$R$^2$ by reaction with the secondary amine of the formula (II) in the presence of a base and in the presence or absence of a solvent.

An ortho-nitrochlorobenzene of the formula (1) in which X is F can be used successfully.

The secondary amine of the formula (2) is dimethylamine, diethylamine, di-n-propylamine, di-i-propylamine, di-n-butylamine, di-i-butylamine, piperidine, morpholine or piperazine, in particular piperidine, morpholine or piperazine, preferably morpholine or piperazine.

Piperidine, morpholine and piperazine are examples of secondary amines of the formula (2) in which $R_1$ and $R^2$, together with the N atom to which they are bonded, form a ring. In each case, this ring has 6 members.

In the first step, the base used is, as already mentioned above, the secondary amine of the formula (2) or a tertiary amine, in particular the secondary amine of the formula (2) or a trialkylamine whose radicals are identical or different and contain from 1 to 25, in particular from 6 to 25, preferably from 8 to 12, carbon atoms per alkyl radical, preferably N-triisooctylamine, trialkyl($C_8/C_{10}$)amines, tri-N-dodecylamine or a mixture thereof.

Particularly suitable bases which form hydrochlorides that are insoluble in water and soluble in the organic phase are trialkylamines having from 7 to 12 carbon atoms per alkyl radical, the alkyl radicals being identical or different, preferably triisooctylamine, trialkyl($C_8/C_{10}$)amines (a mixture of trialkylamines having from 8 to 10 carbon atoms per alkyl radical, for example Hostarex A 327, a commercial product from Hoechst AG) and tri(N-dodecyl)amine. These trialkylamines are particularly suitable as the base for the first step of the reaction sequence.

In the first step of the reaction sequence, the base is used in an amount of from 50 to 500 mol-%, in particular from 100 to 250 mol-%, preferably from 100 to 130 mol-%, based on the number of equivalents of Cl or F to be eliminated.

The purpose of the base is to bind the hydrogen fluoride or hydrogen chloride which forms during the reaction. The base used can be the secondary amine, in which case the latter should be used in an appropriate excess. It is, however, also possible, as indicated previously, to use a tertiary amine, in particular a trialkylamine, as the base. When the reaction is complete, the salts formed from the base are separated off, for example by filtration or decantation, or the reaction product is treated with aqueous alkaline solution, for example aqueous NaOH and/or KOH solution, the secondary or tertiary amine used as the base is freed and he aqueous NaF- and/or KF- or NaCl- and/or KCl-containing solution is separated off.

This variant is particularly advantageous since, firstly, it is very simple to carry out—phase separation involves less work than filtration—and, secondly, the secondary or tertiary amine used as base remains in the reaction product and passes therewith into the next stage, which is likewise carried out in the presence of a base.

The 2-chloro-4-dialkylamino-5-fluoronitrobenzene can be isolated from the resulting reaction mixture and then processed further in isolated form. It is, however, also possible to process further the resulting reaction mixture directly.

In a further variant, ≧200 mol-% of tertiary amine, based on the orthonitrochlorobenzene of the formula (1), is used as base in the first step, meaning that it is possible to use and hydrogenate the resulting reaction mixture directly in the second step, without treatment with aqueous alkaline solution.

If 2,4-dichloro-5-fluoronitrobenzene (X=Cl) is used as starting material, it is recommended to separate off the desired 2-chloro-4-dialkylamino-5-fluoronitrobenzene, for example by crystallization, and proceed using the purified product.

The process according to the invention can be carried out particularly successfully, as mentioned previously, using an ortho-nitrochlorobenzene of the formula (1) in which X=F since, if 2-chloro-4,5-difluoronitro-benzene (X=F) is used as starting material, isolation of the 2-chloro-4-dialkylamino-5-fluoronitrobenzene can be omitted and the reaction mixture resulting in the first step can, following treatment with aqueous alkaline solution, be further processed directly. This variant of the process according to the invention is particularly advantageous since it can be carried out particularly easily. If ≧200 mol-% of tertiary amine, based on 2-chloro-4,5-difluoronitrobenzene, is used as base in the first step, it is possible to use and hydrogenate the resulting reaction mixture directly in the second step, without treatment with aqueous alkaline solution.

If an ortho-nitrochlorobenzene of the formula (1) in which X is F, i.e. 2-chloro-4,5-difluoronitrobenzene, is used, the solvent can be one of those specified above, in particular toluene, ortho-xylene, meta-xylene, para-xylene, a mixture of isomeric xylenes, $(C_1-C_4)$alkyl acetate or a mixture of these solvents.

If, on the other hand, an ortho-nitrochlorobenzene of the formula (1) in which X is Cl, i.e. 2,4-dichloro-5-fluoronitrobenzene, is used, then it is recommended that the solvent used is a dipolar aprotic solvent, e.g. dimethylformamide, dimethylacetamide, 1,3-dimethylimidazolidin-2-one or a mixture thereof.

As already mentioned, the process can be carried out in the presence or absence of a solvent.

In a large number of cases, preference is given to using a solvent both in the first step and also in the second step. A large number of different solvents are suitable for carrying out the process, including nonpolar solvents, aprotic solvents, dipolar aprotic solvents and polar aprotic solvents.

Without laying claim to completeness, it may be mentioned that the solvent used can be an aliphatic hydrocarbon having from 5 to 25 carbon atoms, an aromatic hydrocarbon having from 6 to 12 carbon atoms, an aliphatic alcohol having from 1 to 12 carbon atoms, a polyalkylene glycol having from 2 to 6 carbon atoms per alkylene, a dialkyl ether having from 2 to 20 carbon atoms per alkyl radical, a polyalkylene glycol dialkyl ether having from 1 to 6 carbon atoms per alkylene, a dialkylcarboxamide, a dialkyl sulfoxide, a dialkyl sulfone, an imidazolidinone, a pyrrolidone or a mixture thereof.

Solvents which have been used successfully are benzene, toluene, ortho-xylene, meta-xylene, para-xylene, a technical-grade mixture of isomeric xylenes, ethylbenzene, mesitylene, methanol, ethanol, n-propanol, i-propanol, n-butanol, i-butanol, methyl acetate, ethyl acetate, butyl acetate, dimethylformamide, diethylformamide, dimethylacetamide, diethylacetamide, dimethyl sulfoxide, dimethyl sulfone, sulfolane, 1,3-dimethylimidazolidin-2-one, N-pyrrolidone or a mixture thereof, in particular toluene, ortho-xylene, meta-xylene, para-xylene, a technical-grade mixture of isomeric xylenes, methyl acetate, ethyl acetate, butyl acetate, dimethylformamide, dimethylacetamide, 1,3-dimethylimidazolidin-2-one or a mixture thereof, preferably toluene, ortho-xylene, meta-xylene, para-xylene, a technical-grade mixture of isomeric xylenes or butyl acetate.

In a number of cases, it has proven successful, in the first step of the reaction sequence, to carry out the reaction of the compound of the formula (1) with the secondary amine of the formula (2) at from 0 to 100° C.

For the sake of completeness, it should at this point be pointed out that the reaction to be carried out in the subsequent second step can be carried out in the presence of the same base and the same solvent as in the first step. Accordingly, it is sensible to carry out the reactions in the first and second step in the presence of one and the same base and one and the same solvent. Since the base in the first step is not consumed, but can be freed from the hydrohalide and fed to the reaction taking place in the second step, additional steps to remove or work-up the base and solvent are not required.

In the second step the 2-chloro-4-dialkylamino-5-fluoronitrobenzene resulting from the first step is hydrogenated in the presence of a base and a noble-metal catalyst. The nitro group is converted into an $NH_2$ group and the chlorine which is in the ortho-position relative to the nitro group is also cleaved off to form hydrogen chloride. The purpose of the base is to bind the freed hydrogen chloride.

The base used in the second step is usually the same base as in the first step, namely the secondary amine of the formula (2) or a tertiary amine, in particular the secondary amine of the formula (2) or a trialkylamine whose radicals are identical or different and contain from 1 to 25, in particular from 6 to 25, preferably from 8 to 12 carbon atoms per alkyl radical, preferably triisooctylamine, trialkyl($C_8$/$C_{10}$)amines, tri-n-dodecylamine or a mixture thereof.

Particularly suitable bases for the second step of the reaction sequence are trialkylamines which form hydrochlorides which are insoluble in water and soluble in the organic phase. These include the trialkylamines which have already been specified in the first step of the reaction sequence and which have from 7 to 12 carbon atoms per alkyl radical, the alkyl radicals being identical or different, in particular triisooctylamine, trialkyl($C_8$/$C_{10}$)amines (a mixture of trialkylamines having from 8 to 10 carbon atoms per alkyl radical, for example Hostarex A 327, a commercial product from Hoechst AG) and tri(N-dodecylamine).

The base is used in an amount of from 50 to 500 mol-%, in particular from 100 to 250 mol-%, preferably from 100 to 130 mol-%, based on the number of equivalents of chlorine to be eliminated.

The purpose of the base is to bind the hydrogen chloride eliminated during the reductive dechlorination reaction.

The noble-metal catalyst used is a supported palladium catalyst. The noble-metal catalyst contains from 0.1 to 25%, in particular from 0.5 to 10%, preferably from 1.0 to 5.0% by weight of palladium.

The noble-metal catalyst contains activated carbon, calcium carbonate, barium sulfate, pumice, alumina, kieselguhr, silica gel, aluminum oxide or a mixture thereof, in particular activated carbon, kieselguhr, aluminum oxide or a mixture thereof, preferably activated carbon, as support material.

The hydrogenation reaction is carried out in the presence of hydrogen, in a large number of cases at a pressure of from 2 to 50 bar, in particular at a pressure of from 5 to 30 bar, and at a temperature of from 40 to 140° C., in particular from 60 to 130° C.

When carrying out the second step of the reaction sequence, it must be ensured that the solvent used is inert under the hydrogenation conditions. Unsuitable solvents are chlorinated aliphatic or aromatic hydrocarbons since these can react with hydrogen under the reaction conditions. These limitations regarding the solvent apply only to the hydrogenation stage. In order to avoid changing the solvent, it is advantageous to carry out the first step of the reaction sequence using a solvent which is also suitable for the second step of the reaction sequence.

Examples of suitable solvents are the solvents already specified above.

If a base which, together with the freed hydrogen chloride, forms a hydrochloride which is insoluble in the organic phase, is used then it is recommended to remove this hydrochloride, for example by filtration, and then, as already mentioned, to add an aqueous solution of an acid to the organic phase.

The free base can be recovered from the separated-off hydrochloride in a separate step by adding aqueous alkaline solution and returned to the process.

It is particularly favorable to use a base which, together with the freed hydrogen chloride, forms hydrochlorides which are insoluble in water but soluble in the organic phase. Upon subsequent treatment of the organic phase containing the desired product with an aqueous solution of an acid, these water-insoluble hydrochlorides do not in fact pass into the aqueous phase, but remain in the organic phase and are separated off therewith.

The separated-off organic phase, which, in addition to the hydrochloride of the base, may contain excess base and solvent, is treated with aqueous alkaline solution, as a result of which the free base is formed from the hydrochloride of the base. The freed base remains in the organic phase and can, if a solvent which is insoluble or only sparingly soluble in water has been used in the first step of the reaction sequence, be separated off together with the solvent and, where necessary after purification, be returned to the process according to the invention. This means that the tertiary amine used as base can be recycled without any appreciable losses. The auxiliaries are only consumed when the base is freed from its salts, in which case a corresponding amount of alkali in the form of an aqueous NaOH or KOH solution is consumed.

The reaction mixture produced after hydrogenation has taken place is, if necessary after the noble-metal catalyst has been removed, admixed in a third step with an aqueous solution of an acid, a water-soluble salt of the corresponding 3-fluoro-4-dialkylaminoaniline being formed and transferred to the aqueous phase.

The acid used is a mineral acid, for example hydrochloric acid or sulfuric acid, in particular hydrochloric acid. The aqueous solution of the acid usually contains from 1 to 30% by weight, in particular from 5 to 15% by weight, of acid.

The aqueous phase is then separated off from the organic phase and, if necessary, from the noble-metal catalyst, which should now be removed if previous removal has been omitted.

It is not necessary to isolate the desired product (3-fluoro4-dialkylaminoaniline) at this point in the process in order to process it further in isolated form. On the contrary, it is an advantage of the process according to the invention to omit isolation of the desired product, for example by crystallization and/or distillation, at this point and merely to carry out phase separation instead.

The 3-fluoro-4-dialkylaminoaniline salt dissolved in water is then reacted with the chloroformate in the presence of the basic compound.

The basic compound used may be an oxide, carbonate or hydrogencarbonate of an alkali metal or alkaline earth metal or an amine or a mixture thereof, in particular an alkali metal hydrogencarbonate, an alkali metal carbonate or a mixture thereof, preferably an alkali metal hydrogencarbonate or a mixture thereof. Particular success has been achieved using sodium hydrogencarbonate and/or potassium hydrogencarbonate.

The basic compound can be used without a diluent or in the form of a solution, in particular in the form of an aqueous solution.

It is customary to use from 50 to 300, in particular from 150 to 250, preferably from 200 to 220, equivalents of basic compound per mole of formate of the formula (3).

Examples of suitable chloroformates are alkyl chloroformates having from 1 to 4 carbon atoms in the alkyl radical, benzyl chloroformate, in particular methyl chloroformate, ethyl chloroformate, n-propyl chloroformate, i-propyl chloroformate, n-butyl chloroformate, i-butyl chloroformate, benzyl chloroformate, preferably benzyl chloroformate.

The basic compound is used to free the corresponding 3-fluoro-4-dialkyl-aminoaniline from the water-soluble salt, to bind the hydrogen chloride produced in the reaction and, where necessary, to neutralize excess acid still present. In this way, it is also ensured that N-carboxyalkyl-3-fluoro-4-dialkylaminoaniline salts, which may be water-soluble and would remain in the aqueous solution, are not formed. This simplifies removal of the desired N-carboxyalkyl-3-fluoro-4-dialkylaminoaniline from the aqueous phase, for example by filtration.

In a particular process variant, the aqueous solution of the water-soluble 3-fluoro-4-dialkylaminoaniline salt is introduced and the chloroformate and the basic compound are added simultaneously, but separately, whilst mixing well. This variant has the advantage that it is particularly easy to carry out.

Since the resulting amine hydrochloride is usually water-soluble, with this variant, it is possible, in a particularly advantageous way, to dispense with the presence of an organic solvent.

In most cases it has proven to be sufficient to carry out the reaction with the chloroformate at from 10 to 80° C.

When the reaction is complete, the N-carboxyalkyl-3-fluoro4-dialkylaminoaniline is usually obtained as a solid, which precipitates out of the aqueous phase and may be removed by filtration and/or extraction using an organic solvent which is insoluble in water. If wished, the desired product can be subjected to further purification, although it is generally produced in sufficiently high purity.

The process can be carried out at subatmospheric pressure, atmospheric pressure or superatmospheric pressure.

It is suited to both continuous and also batch processing.

The present invention further relates to the compounds 2-chloro-4-diethylamino-5-fluoronitrobenzene, 2-chloro-5-fluoro-4-morpholinonitrobenzene, 2-chloro-5-fluoro-10 4-piperidinonitrobenzene and 2-chloro-5-fluoro4-piperazinonitrobenzene, in particular to 2-chloro-5-fluoro-4-morpholinonitrobenzene and 2-chloro-5-fluoro-4-piperazinonitrobenzene.

The present invention further relates to the compounds 2-chloro-5-fluoro-4-morpholinoaniline and 2-chloro-5-fluoro-4-piperazinoaniline. Of particular interest are the compounds 2-chloro-5-fluoro-4-morpholinonitrobenzene and 2-chloro-5-fluoro-4-morpholinoaniline.

All of the compounds specified above are valuable intermediates in the preparation of N-carboxyalkyl-3-fluoro-4-dialkylaminoanilines.

The following examples describe the invention in more detail without representing a limitation.

Experimental part

EXAMPLE 1

Preparation of N-carboxybenzyl-3-fluoro-4-morpholinoaniline 58.1 g (0.3 mol) of 2-chloro-4,5-difluoronitrobenzene, 120 ml of toluene and 180 g (about 0.45 mol) of tri-N(octyl/decyl)amine (a mixture of trialkyl($C_8/C_{10}$)amines) are introduced, with stirring, into a 1000 ml three-necked flask fitted with stirrer, thermometer and reflux condenser, and heated to 50° C. 31.3 g (0.36 mol) of morpholine are added over the course of one hour.

The mixture is then stirred at 50° C. for a further 5 hours, 666 g of toluene are added and the mixture is heated to 80° C. With thorough mixing, 66 g of a 20% by weight aqueous sodium hydroxide solution are then added and the aqueous phase is separated off.

The organic phase which is obtained after separating off the aqueous phase is transferred, together with 3.9 g of a palladium catalyst (5% by weight of palladium on activated carbon, 50% by weight water-moist), to a 2 l stirred autoclave under nitrogen protection. The autoclave is maintained under nitrogen atmosphere and closed after charging.

The mixture is heated to 95° C. with stirring, and hydrogen at a pressure of 30 bar is added at this temperature until no more hydrogen is absorbed. The pressure in the autoclave is released and the catalyst is removed by filtering off using a suction filter.

The reaction solution which is produced following removal of the catalyst is admixed with a solution prepared from 65 g of a 37% by weight hydrochloric acid and 420 g of water, and the desired product is transferred into the aqueous phase. The aqueous phase is then separated off at room temperature and 693 g (0.66 mol) of $NaHCO_3$ (aqueous solution containing 8% by weight of $NaHCO_3$) and 56.0 g (0.33 mol) of benzyl chloroformate are then added separately, but simultaneously, over the course of one hour.

When addition is complete, the mixture is stirred for a further one hour. The solid formed is then filtered off with suction, washed with water and subsequently dried.

All of the reaction steps are carried out under inert-gas protection (nitrogen).

82.4 g (0.25 mol) of N-carboxybenzyl-3-fluoro-4-morpholinoaniline are produced, corresponding to a yield of 83.3%, based on 2-chloro-4,5-difluoronitrobenzene used.

EXAMPLE 1a

Preparation of 2-chloro-5-fluoro-4-morpholinonitrobenzene

A solution of 4.8 g (25 mmol) of 2-chloro4,5-difluoronitrobenzene in 10.6 g of toluene is introduced into a 100 ml three-necked flask fitted with dropping funnel, precision-ground glass stirrer and reflux condenser. 4.4 g (50 mmol) of morpholine are added dropwise to this solution at room temperature and with stirring over the course of 1 hour. The mixture is then stirred for a further 2 hours at room temperature and the reaction products formed during the reaction are filtered off with suction.

The filter cake is washed three times with 10 ml of water in each case and then dried to give 5.7 g (22.1 mmol) of 2-chloro-5-fluoro-4-morpholinonitrobenzene. This corresponds to a yield of 89.1%, based on 2-chloro-5-fluoro-4-morpholinonitrobenzene used.

2-Chloro-5-fluoro-4-morpholinonitrobenzene of the following formula

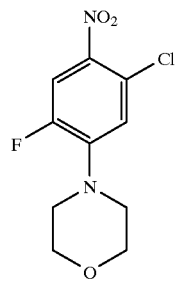

has a melting point of 164.9° C.

$^1$H-NMR: δ(TMS)=0, ($CDCl_3$): δ=3.28 (br, t); 3.87 (br, t, 4.7 Hz); 6.93 (d, $J_{F,C}$=7.8 Hz)7.81 (d, $J_{F,C}$=12.8 Hz).

$^{13}$C-NMR: δ($CDCl_3$)=77, ($CDCl_3$): δ=49.63 (t, $J_{F,C}$=5.14 Hz); 66.38 (t, $J_{F,C}$<0.7 Hz); 114.97 (d, $J_{F,C}$=27.76 Hz); 119.76 (d, $J_{F,C}$=3.90 Hz); 124.92 (s, $J_{F,C}$=3.17 Hz); 138.51 (br, s, $J_{F,C}$=8.21 Hz); 144.27 (s, $J_{F,C}$=8.45 Hz); 151.27 (s, $J_{F,C}$=250.05 Hz).

$^{19}$F-NMR: δ[$CFCl_3$ (virt. int.)]=0, ($CDCl_3$): δ=−121.14 (s).

EXAMPLE 1b

Preparation of 2-chloro-5-fluoro-4-morpholinoaniline

A 2 l stirred autoclave is charged with 78.2 g (0.3 mol) of 2-chloro-5-fluoro-4-morpholinonitrobenzene together with 3.9 g of a platinum/activated carbon catalyst (5% by weight of Pt, 50% by weight water content, sulfited) in 782 g (10.2 mol) of toluene at a temperature of 70° C. The autoclave is closed and rendered inert using nitrogen. The reaction temperature is raised to 80° C. and a hydrogen pressure of 5 bar is maintained at this temperature until the hydrogen absorption decreases sharply.

After the catalyst has been filtered off with suction, the reaction product 2-chloro-5-fluoro-4-morpholinoaniline is further used for the following stage without further purification.

Alternatively, the solvent is evaporated and the 2-chloro-5-fluoro-4-morpholinoaniline is precipitated and purified. This method gives 57.4 g (0.25 mol) of 2-chloro-5-fluoro-4-morpholinoaniline, corresponding to 83.3% of the theoretical yield, based on 2-chloro-5-fluoro-4-morpholinonitrobenzene used. Melting point: 89.5° C.

$^1$H-NMR: δ(TMS)=0, ($CDCl_3$):δ=2.95 ($m_c$); 3.84 ($m_c$); 3.90 (br, s); 6.51 (d, $J_{F,H}$=13.0 Hz), 6.87 (d, $J_{F,H}$=8.4 Hz).

$^{13}$C-NMR: δ($CDCl_3$)=77, ($CDCl_3$): δ=51.59 (t, $J_{F,C}$=2.6 Hz); 67.00 (t); 104.15 (d, $J_{F,C}$=25.5 Hz); 113.90 (s, $J_{F,C}$=3.0 Hz); 120.29 (d, $J_{F,C}$=4.4 Hz); 132.20 (s, $J_{F,C}$=11.1 Hz); 138.78 (s, $J_{F,C}$=10.8 Hz); 155.39 (s, $J_{F,C}$=245.4 Hz).

EXAMPLE 2

Preparation of N-carboxybenzyl-3-fluoro-4-morpholinoaniline starting from 2,4-dichloro-5-fluoronitrobenzene.

130.0 g (0.62 mol) of 2,4-dichloro-5-fluoronitrobenzene and 260 ml of N,N-dimethylacetamide are introduced, with stirring, into a 1000 ml three-necked flask fitted with stirrer, thermometer and reflux condenser, and 113.3 g (1.3 mol) of morpholine are added at 25° C. over the course of 2 hours.

The mixture is then stirred at 25° C. for a further 16 hours. A total of 235 ml of solvent (N,N-dimethylacetamide) are then distilled off at 25 mbar. The 2-chloro-5-fluoro-4-morpholinonitrobenzene-containing residue which remains is quickly filtered off using a suction filter and washed with toluene and water and dried.

The dried residue, which already contains 2-chloro-5-fluoro-4-morpholino-nitrobenzene in a purity of ≧95%, is taken up in 666 g of toluene and, after 3.9 g of a palladium catalyst (5% by weight of palladium on activated carbon, 50% by weight water-moist) have been added, is processed further as described in Example 1.

79.6 g (0.24 mol) of N-carboxybenzyl-3-fluoro-4-morpholinoaniline are obtained, corresponding to a yield of 48.2%, based on 2,4-dichloro-5-nitrobenzene used.

EXAMPLE 3

Preparation of N-carboxybenzyl-3-fluoro-4-piperazinoaniline 97.0 g (0.5 mol) of 2-chloro-4,5-difluoronitrobenzene and 284 g of toluene are introduced, with stirring, into a 1000 ml three-necked flask fitted with stirrer, thermometer and reflux condenser, and heated to 50° C. and 94.8 g (1.1 mol) of piperazine are added over the course of one hour.

The mixture is then stirred at 50° C. for a further 2 hours and heated to 80° C. 200 g of a 10% by weight aqueous sodium hydroxide solution are then added, with thorough mixing, and the aqueous phase is then separated off.

The organic phase which is obtained after the aqueous phase has been separated off is transferred, together with 3.9 g of a palladium catalyst (5% by weight of palladium on activated carbon, 50% by weight water-moist) and 300 g of tri-N-(octyl-/decyl-)amine (a mixture of trialkyl($C_8/C_{10}$) amines, under nitrogen to a 2 l autoclave. The autoclave is maintained under nitrogen and closed after charging.

The mixture is heated to 95° C. with stirring, and hydrogen at a pressure of 30 bar is added at this temperature until no more hydrogen is absorbed. The pressure in the autoclave is released and the catalyst is removed using a suction filter.

The reaction solution which results following removal of the catalyst is extracted with a total of 547 g of 10% aqueous hydrochloric acid, and the aqueous phase is separated off.

1940 g (0.44 mol) of $NaHCO_3$ (10% aqueous solution) and 187.6 g (1.1 mol) of benzyl chloroformate are added to the aqueous phase simultaneously, but separately, at room temperature over the course of one hour.

When addition is complete, the mixture is stirred for a further one hour. The solid formed is then filtered off with suction, washed with water and subsequently dried.

All of the reaction steps are carried out under an inert-gas protection (nitrogen).

187.5 g (0.4 mol) of N-carboxybenzyl-3-fluoro4-piperazinoaniline are obtained, corresponding to a theoretical yield of 81.0%, based on 2-chloro-4,5-difluoronitrobenzene used.

EXAMPLE 3a

Preparation of 2-chloro-5-fluoro-4-piperazinonitrobenzene

A solution of 19.3 g (0.08 mol) of 2-chloro-4,5-difluoronitrobenzene in 100 g of toluene are introduced into a 200 ml three-necked flask fitted with dropping funnel, precision-ground glass stirrer and reflux condenser. 18.1 g (0.21 mol) of piperazine are added dropwise to this solution at room temperature and with stirring over the course of one hour. The mixture is then stirred at room temperature for a further 2 hours. The reaction solution formed during the reaction is washed three times with 20 ml of water in each case and dried. The solvent is removed to give 18.5 g (0.071 mmol) of 2-chloro-5-fluoro-4-piperazinonitrobenzene. This corresponds to a yield of 95%, based on 2-chloro-4,5-difluoronitrobenzene used. 2-Chloro-5-fluoro-4-piperazinonitrobenzene of the following formula

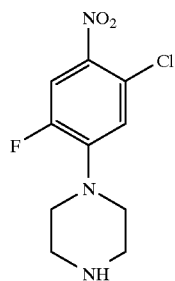

has a melting point of 91.5° C. (purity: 92.9%, determined by HPLC).

$^1$H-NMR: δ(TMS)=0, ($CDCl_3$): δ=1.81 (d); 3.04 ($m_c$); 3.26 ($m_c$); 6.91 (d, $J_{F,C}$=7.9 Hz); 7.80 (d, $J_{F,C}$=12.9 Hz).

$^{13}$C-NMR: δ($CDCl_3$)=77, ($CDCl_3$): δ=45.81 (t); 50.71 (t, $J_{F,C}$=5.2 Hz); 114.97 (d, $J_{F,C}$=27.9 Hz); 119.91 (d, $J_{F,C}$=4.1 Hz); 124.95 (s, $J_{F,C}$=3.1 Hz); 138.51 (s, $J_{F,C}$=8.5 Hz); 144.80 (s, $J_{F,C}$=8.4 Hz); 151.24 (s, $J_{F,C}$=249.9 Hz).

EXAMPLE 3b

Preparation of 2-chloro-5-fluoro-4-piperazinoaniline 77.8 9 (0.3 mol) of 2-chloro-5-fluoro-4-piperazinonitrobenzene are used together with 3.9 g of a platinum/activated carbon catalyst (5% by weight of Pt; 50% by weight water content, sulfited) in 782 g (10.2 mol) of toluene and processed as described in Example 1.

54.1g (0.24 mol) of 2-chloro-5-fluoro-4-piperazinoaniline are obtained, corresponding to 78.2% of the theoretical yield, based on 2-chloro-5-fluoro-4-piperazinonitrobenzene used.

Melting point: 110° C. (95% strength)

$^1$H-NMR: δ(TMS)=0, ($CDCl_3$): δ=1.67 ($m_c$); 3.88 ($m_c$), 3.90 (br, s); 6.50 (d, $J_{F,H}$=13.0 Hz), 6.87 (d, $J_{F,H}$=8.4 Hz).

$^{13}$C-NMR: δ($CDCl_3$)77, ($CDCl_3$): δ=46.24 (t, $J_{F,C}$=0 Hz); 52.62 (t, $J_{F,C}$=2.3 Hz); 104.10 (d, $J_{F,C}$=25.6 Hz); 113.85 (s, $J_{F,C}$=2.9 Hz); 120.47 (d, $J_{F,C}$=4.4 Hz); 132.94 (s, $J_{F,C}$=10.8 Hz); 138.52 (s, $J_{F,C}$=10.7 Hz); 155.40 (s, $J_{F,C}$=245.4 Hz).

EXAMPLE 4

Preparation of 2-chloro4-diethylamino-5-fluoronitrobenzene

A solution of 4.8 g (25 mmol) of 2-chloro-4,5-difluoronitrobenzene in 14.4 g of toluene are introduced into a 100 ml three-necked flask fitted with dropping funnel, precision-ground glass stirrer and reflux condenser. 5.7 g (78 mmol) of diethylamine are added dropwise to this solution at room temperature and with stirring over the course of 1 hour. The mixture is then stirred at room temperature for a further 2 hours. The reaction solution formed in the reaction is washed three times with 35 ml of water in each case and dried. The solvent is removed to give 5.4 g (22 mmol) of 2-chloro-4-diethylamino-5-fluoronitrobenzene. This corresponds to a yield of 88%, based on 2-chloro-4,5-difluoronitrobenzene used.

Melting point: 68.9° C.

$^1$H-NMR: δ(TMS)=0, ($CDCl_3$): δ=1.24 (td, $J_{F,H}$=0.5 Hz); 3.44 (qd, $J_{F,H}$=1.5 Hz); 6.72 (d, $J_{F,H}$=8.3 Hz); 7.83 (d, $J_{F,H}$=14.6 Hz).

$^{13}$C-NMR: δ($CDCl_3$)=77, ($CDCl_3$): δ=13.04 (q, $J_{FC}$=1.9 Hz); 46.42 (t, $J_{F,C}$=6.2 Hz); 115.70 (d, $J_{F,C}$=29.2 Hz); 117.06 (d, $J_{F,C}$=5.3 Hz); 125.67 (s, $J_{F,C}$=2.3 Hz); 134.37 (s, $J_{F,C}$=8.0 Hz); 142.25 (s, $J_{F,C}$=8.3 Hz); 148.48 (s, $J_{F,C}$=245.9 Hz).

EXAMPLE 5
Preparation of 2-chloro-5-fluoro-4-piperidinonitrobenzene

A solution of 4.8 (25 mmol) of 2-chloro-4,5-difluoronitrobenzene in 14.4 g of toluene is introduced into a 100 ml three-necked flask fitted with dropping funnel, precision-ground glass stirrer and reflux condenser. 4.3 g (50 mmol) of piperidine are added dropwise to this solution at room temperature and with stirring over the course of 1 hour. The mixture is then stirred at room temperature for a further 2 hours. The reaction solution formed in the reaction is washed three times with 35 ml of water in each case and dried. Removal of the solvent gives 5.3 g (21 mmol) of 2-chloro-5-fluoro-4-piperidinonitrobenzene. This corresponds to a yield of 82.0%, based on 2-chloro-4,5-difluoronitrobenzene used.

2-Chloro-5-fluoro-4-piperidinonitrobenzene of the following formula

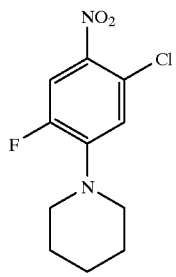

has a melting point of 70° C. (purity: 99.5%, determined by HPLC).

$^1$H-NMR: δ(TMS)=0, (CDCl$_3$): δ=1.66 (m$_c$); 1.72 (m$_c$); 3.27 (t, 5.4 Hz); 6.90 (d, J$_{F,H}$=8.0 Hz); 7.79 (d, J$_{F,H}$=13.1 Hz).

$^{13}$C-NMR: δ(CDCl$_3$)=77, (CDCl$_3$): δ=23.96 (t, J$_{F,C}$=0.8 Hz); 25.66 (t) 1144.97 (d, J$_{F,C}$=28.1 Hz); 119.91 (d, J$_{F,C}$=4.2 Hz); 125.01 (s, J$_{F,C}$=2.9 Hz); 137.39 (s, J$_{F,C}$=8.5 Hz); 145.11 (s, J$_{F,C}$=8.4 Hz); 151.04 (s, J$_{F,C}$=249.4 Hz).

We claim:

1. A process for the preparation of N-carboxyalkyl-3-fluoro-4-dialkylaminoanilines, which comprises reacting, in a first step, an ortho-nitrochlorobenzene of the formula (1)

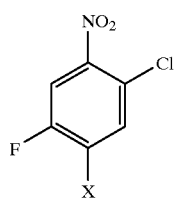

(1)

in which X is Cl or F, with a secondary amine of the formula (2) HNR$^1$R$^2$, in which R$^1$ and R$^2$, independently of one another, are identical or different and are an alkyl radical having from 1 to 10 carbon atoms or, together with the N atom to which they are bonded, form a ring having from 3 to 7 members, in the presence of a base in the presence or absence of a solvent at from −10 to 120° C., reacting, in a second step, the 2-chloro-4-dialkylamino-5-fluoronitrobenzene with hydrogen at from 30 to 150° C. and from 1 to 100 bar in the presence of a base and a noble-metal catalyst and, in a third step, extracting the 3-fluoro-4-dialkylaminoaniline from the reaction mixture using an aqueous solution of an acid as a salt dissolved in water, removing the aqueous phase and reacting the 3-fluoro4-dialkylaminoaniline salt, dissolved in water, with a chloroformate of the formula (3) ClCO$_2$R$^3$, in which R$^3$ is an alkyl radical having from 1 to 10 carbon atoms or an aralkyl radical having from 7 to 20 carbon atoms, at from 0 to 100° C. in the presence of a basic compound.

2. The process as claimed in claim 1, wherein the secondary amine of the formula (2) is dimethylamine, diethylamine, di-n-propylamine, di-i-propylamine, di-n-butylamine, di-i-butylamine, piperidine, morpholine or piperazine.

3. The process as claimed in claim 1, wherein the base used in the first step is the secondary amine of the formula (2) or a tertiary amine.

4. The process as claimed in claim 1, wherein the base used in the first step is a trialkylamine whose radicals are identical or different and contain from 1 to 25 carbon atoms per alkyl radical.

5. The process as claimed in claim 1, wherein the base is used in the first step in an amount of from 50 to 500 mol-%, based on the number of equivalents of chlorine or fluorine to be eliminated.

6. The process as claimed in claim 1, wherein the solvent used is an aliphatic hydrocarbon having from 5 to 25 carbon atoms, an aromatic hydrocarbon having from 6 to 12 carbon atoms, an aliphatic alcohol having from 1 to 12 carbon atoms, a polyalkylene glycol having from 2 to 6 carbon atoms per alkylene, a dialkyl ether having from 2 to 20 carbon atoms per alkyl radical, a polyalkylene glycol dialkyl ether having from 1 to 6 carbon atoms per alkylene, a dialkylcarboxamide, a (C$_1$–C$_4$)alkyl acetate, a nitrile, a dialkyl sulfoxide, a dialkyl sulfone, an imidazolinone, a pyrrolidone or a mixture thereof.

7. The process as claimed in claim 1, wherein the base used in the second step is the secondary amine of the formula (2) or a tertiary amine.

8. The process as claimed in claim 1, wherein the base used in the second step is a trialkylamine whose radicals are identical or different and contain from 1 to 25 carbon atoms per alkyl radical.

9. The process as claimed in claim 1, wherein the base is used in the second step in an amount of from 50 to 500 mol-%, based on the number of equivalents of chlorine to be eliminated.

10. The process as claimed in claim 1, wherein the noble-metal catalyst used is a supported palladium catalyst.

11. The process as claimed in claim 1, wherein the acid used is a mineral acid.

12. The process as claimed in claim 1, wherein the basic compound used is an oxide, carbonate or hydrogencarbonate of an alkali metal or alkaline earth metal or an amine or a mixture thereof.

13. The process as claimed in claim 1, wherein from 2 to 3 equivalents of basic compound are used per mole of chloroformate of the formula (3).

* * * * *